United States Patent
Golenberg et al.

(10) Patent No.: US 11,571,515 B2
(45) Date of Patent: Feb. 7, 2023

(54) CONTROLLING MEDICAL DEVICE OPERATION AND FEATURES BASED ON DETECTED PATIENT SLEEPING STATUS

(71) Applicant: MEDTRONIC MINIMED, INC., Northridge, CA (US)

(72) Inventors: Lavie Golenberg, Singapore (SG); Louis J. Lintereur, Boise, ID (US); Benyamin Grosman, Winnetka, CA (US); Di Wu, Palo Alto, CA (US); Maria Diana Miller, Santa Rosa Valley, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 251 days.

(21) Appl. No.: 17/005,929

(22) Filed: Aug. 28, 2020

(65) Prior Publication Data

US 2021/0060248 A1    Mar. 4, 2021

Related U.S. Application Data

(60) Provisional application No. 62/947,942, filed on Dec. 13, 2019, provisional application No. 62/893,722, filed on Aug. 29, 2019.

(51) Int. Cl.
*A61M 5/172* (2006.01)
*A61B 5/00* (2006.01)
*A61M 5/142* (2006.01)

(52) U.S. Cl.
CPC ......... *A61M 5/1723* (2013.01); *A61B 5/4809* (2013.01); *A61B 5/746* (2013.01);
(Continued)

(58) Field of Classification Search
None
See application file for complete search history.

(56) References Cited

U.S. PATENT DOCUMENTS

| 4,562,751 A | 1/1986 | Nason et al. |
| 4,685,903 A | 8/1987 | Cable et al. |

(Continued)

FOREIGN PATENT DOCUMENTS

| EP | 3567594 | 11/2019 |
| WO | 2020072128 | 4/2020 |

OTHER PUBLICATIONS

Katelijn Vleugels, Automated Detection of a Physical Behavior Event and Corresponding Adjustment of a Physiological Characteristic Sensor Device, U.S. Appl. No. 16/886,360, filed May 28, 2020.

(Continued)

*Primary Examiner* — Manuel A Mendez
(74) *Attorney, Agent, or Firm* — Weaver Austin Villeneuve & Sampson LLP

(57) ABSTRACT

A system includes a medical device that regulates delivery of medication to a user, a sleep detection system configured to generate user status data that indicates sleeping status of the user, and configured to communicate the user status data, and at least one controller that controls alerts associated with operation of the medical device. The at least one controller receives the user status data generated by the sleep detection system, determines, from the user status data, that the user is sleeping, activates a sleep mode alerting scheme of the medical device when it determines that the user is sleeping, and, after activating the sleep mode alerting scheme, controls generation and outputting of alerts associated with operation of the medical device in accordance with the sleep mode alerting scheme.

22 Claims, 7 Drawing Sheets

(52) U.S. Cl.
CPC ..... *A61M 5/14248* (2013.01); *A61M 2205/18* (2013.01); *A61M 2205/505* (2013.01); *A61M 2205/52* (2013.01); *A61M 2205/581* (2013.01); *A61M 2205/582* (2013.01); *A61M 2205/583* (2013.01); *A61M 2205/587* (2013.01); *A61M 2205/8206* (2013.01); *A61M 2230/005* (2013.01); *A61M 2230/201* (2013.01); *A61M 2230/63* (2013.01)

(56) References Cited

U.S. PATENT DOCUMENTS

| | | |
|---|---|---|
| 4,755,173 A | 7/1988 | Konopka et al. |
| 5,080,653 A | 1/1992 | Voss et al. |
| 5,097,122 A | 3/1992 | Colman et al. |
| 5,391,250 A | 2/1995 | Cheney, II et al. |
| 5,485,408 A | 1/1996 | Blomquist |
| 5,505,709 A | 4/1996 | Funderburk et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 3,019,410 A1 | 9/2011 | Bharmi et al. |
| 3,024,201 A1 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 9,037,254 B2 | 5/2015 | John |
| 9,622,675 B2 | 4/2017 | Leyde et al. |
| 10,342,923 B2 | 7/2019 | Henrich et al. |
| 10,593,231 B2 | 3/2020 | Cahan et al. |
| 10,716,896 B2 | 7/2020 | O'Connor et al. |
| 2007/0123819 A1 | 5/2007 | Mernoe et al. |
| 2009/0062730 A1 | 3/2009 | Woo |
| 2010/0160861 A1 | 6/2010 | Causey, III et al. |
| 2013/0046281 A1 | 2/2013 | Javitt |
| 2016/0184518 A1 | 6/2016 | Freeman et al. |
| 2016/0317077 A1 | 11/2016 | Sillay |
| 2017/0164878 A1 | 6/2017 | Connor |
| 2017/0258986 A1 | 9/2017 | Tsoukalis |
| 2018/0174675 A1 | 6/2018 | Roy et al. |
| 2018/0318529 A1 | 11/2018 | Davidson et al. |
| 2018/0353682 A1 | 12/2018 | Laurence et al. |
| 2019/0365286 A1 | 12/2019 | Powers, III et al. |
| 2020/0015739 A1 | 1/2020 | Abraham et al. |
| 2020/0135320 A1 | 4/2020 | Vleugels |
| 2020/0286612 A1 | 9/2020 | Mears |
| 2020/0289373 A1 | 9/2020 | Vleugels |
| 2020/0294645 A1 | 9/2020 | Vleugels |
| 2021/0060249 A1 | 3/2021 | Golenberg et al. |
| 2021/0090727 A1* | 3/2021 | Rosinko ............ G06F 21/84 |
| 2021/0178066 A1 | 6/2021 | Monirabbasi |

OTHER PUBLICATIONS

Carroll, L., "Experimental Phone App Works With Insulin Pumps to Control Diabetes", Reuters, Healthcare & amp; Pharma, Jan. 29, 2019, 8 pages, https://www.reuters.com/article/us-health-diabetes-apps/experimental-phoneapp-works-with-insulin-pumps-to-control-diabetes-idUSKCN1PN32D.

Smith, A., "FDA Approves New Smart Insulin Pump", Oct. 3, 2016, 3 pages.

* cited by examiner

CONTROLLING MEDICAL DEVICE OPERATION AND FEATURES BASED ON DETECTED PATIENT SLEEPING STATUS

CROSS-REFERENCE TO RELATED APPLICATIONS

This application claims the benefit of U.S. provisional patent application No. 62/947,942, filed Dec. 13, 2019. This application also claims the benefit of U.S. provisional patent application No. 62/893,722, filed Aug. 29, 2019.

TECHNICAL FIELD

The present technology is generally related to the control of medical device operation and features, such as alert generation and regulation of therapy delivery.

BACKGROUND

Medical therapy delivery systems, such as fluid infusion devices, are relatively well known in the medical arts, for use in delivering or dispensing an agent, such as insulin or another prescribed medication, to a patient. A typical insulin infusion device includes a fluid pump mechanism and an associated drive system that actuates a plunger or piston of a fluid reservoir to deliver fluid medication from the reservoir to the body of a patient via a fluid delivery conduit between the reservoir and the body of a patient. Use of infusion pump therapy has been increasing, especially for delivering insulin to diabetic patients.

Medical devices, including insulin infusion devices, can be controlled and operated to generate and output (or control the generation and outputting) of various alerts, alarms, messages, and notifications, in different contexts and for different reasons. Some alerts may be merely informative in nature, while other alerts may be more important. For example, alerts related to patient safety, operating health of the medical device, and patient health status may be categorized as high priority, while alerts related to battery charge status, patient reminders or recommendations, and non-critical device status may be categorized as low priority.

Control schemes have been developed to allow insulin infusion devices to monitor and regulate a patient's blood glucose level in a substantially continuous and autonomous manner. An insulin infusion device can be operated in an automatic mode wherein basal insulin is delivered at a rate that is automatically adjusted for the user. While controlling the delivery of basal insulin in this manner, the infusion device can also control the delivery of correction boluses to account for rising glucose trends, a sudden spike or drop in detected blood glucose, etc. Ideally, the amount of a correction bolus should be accurately calculated and administered to maintain the user's blood glucose within the desired range. In particular, an automatically generated and delivered correction bolus should safely manage the user's blood glucose level and keep it above a defined threshold level. To this end, an insulin infusion device operating in an automatic mode uses continuous glucose sensor data and control algorithms to regulate the user's blood glucose, based on a target glucose setpoint setting.

BRIEF SUMMARY

The subject matter of this disclosure generally relates to the regulation and control of certain features and functions of a medical device, such as an insulin infusion device, based on the output of a sleep detection system that monitors the sleeping status of the patient. The disclosed subject matter contemplates the adjustment of a medical device alerting scheme in response to the detected or determined sleeping status of the patient. The disclosed subject matter also contemplates the adjustment of a target glucose setpoint value of an insulin infusion device, in response to the detected or determined sleeping status of the patient.

In one aspect, the present disclosure provides an automated method of controlling alerts associated with operation of a medical device. Embodiments of the method involve: receiving user status data that indicates sleeping status of a user of the medical device, the user status data generated by a sleep detection system; determining, from the user status data, that the user is sleeping; in response to the determining, activating a sleep mode alerting scheme of the medical device; and after activating the sleep mode alerting scheme, controlling generation and outputting of alerts associated with operation of the medical device in accordance with the sleep mode alerting scheme.

In another aspect, the disclosure provides a medical device that regulates delivery of medication to a user. Embodiments of the medical device include: a fluid pump mechanism; at least one controller that regulates operation of the fluid pump mechanism to deliver a fluid medication from the medical device; and at least one memory element associated with the at least one controller. The at least one memory element stores processor-executable instructions configurable to be executed by the at least one controller to perform a method of controlling operation of the medical device. Embodiments of the method involve: receiving user status data that indicates sleeping status of the user, the user status data generated by a sleep detection system; determining, from the user status data, that the user is sleeping; in response to the determining, activating a sleep mode alerting scheme of the medical device; and after activating the sleep mode alerting scheme, controlling generation and outputting of alerts associated with operation of the medical device in accordance with the sleep mode alerting scheme.

In another aspect, the disclosure provides a system having: a medical device that regulates delivery of medication to a user; a sleep detection system configured to generate user status data that indicates sleeping status of the user, and configured to communicate the user status data; and at least one controller that controls alerts associated with operation of the medical device. The at least one controller is configured to: receive the user status data generated by the sleep detection system; determine, from the user status data, that the user is sleeping; in response to determining that the user is sleeping, activating a sleep mode alerting scheme of the medical device; and after activating the sleep mode alerting scheme, control generation and outputting of alerts associated with operation of the medical device in accordance with the sleep mode alerting scheme.

In another aspect, the disclosure provides a method of operating an insulin infusion device having a fluid pump mechanism and at least one controller that regulates operation of the fluid pump mechanism to deliver insulin from the insulin infusion device. Embodiments of the method involve: operating the insulin infusion device in an automatic mode to automatically control delivery of insulin to a user, in accordance with a first target glucose setpoint value; receiving user status data that indicates sleeping status of the user, the user status data generated by a sleep detection system; determining, from the user status data, that the user is sleeping while the insulin infusion device is operating in the automatic mode; in response to the determining, transitioning from the first target glucose setpoint value to a second target glucose setpoint value for use during the automatic mode, the transitioning occurring without user input, and the second target glucose setpoint value different than the first target glucose setpoint value; and continuing to operate the insulin infusion device in the automatic mode to automatically control delivery of insulin to the user, in accordance with the second target glucose setpoint value.

In another aspect, the disclosure provides an insulin infusion device having: a fluid pump mechanism; at least one controller that regulates operation of the fluid pump mechanism to deliver insulin from the insulin infusion device; and at least one memory element associated with the at least one controller, the at least one memory element storing processor-executable instructions configurable to be executed by the at least one controller to perform a method of controlling operation of the insulin infusion device. Embodiments of the method involve: operating the insulin infusion device in an automatic mode to automatically control delivery of insulin to a user, in accordance with a first target glucose setpoint value; receiving user status data that indicates sleeping status of the user, the user status data generated by a sleep detection system; determining, from the user status data, that the user is sleeping while the insulin infusion device is operating in the automatic mode; in response to the determining, transitioning from the first target glucose setpoint value to a second target glucose setpoint value for use during the automatic mode, the transitioning occurring without user input, and the second target glucose setpoint value different than the first target glucose setpoint value; and continuing to operate the insulin infusion device in the automatic mode to automatically control delivery of insulin to the user, in accordance with the second target glucose setpoint value.

In another aspect, the disclosure provides a system having: an insulin infusion device that regulates delivery of insulin to a user; a sleep detection system configured to generate user status data that indicates sleeping status of a user, and configured to communicate the user status data; and at least one controller that controls operation of the insulin infusion device. The at least one controller is configured to: operate the insulin infusion device in an automatic mode to automatically control delivery of insulin to a user, in accordance with a first target glucose setpoint value; receive the user status data generated by the sleep detection system; determine, from the user status data, that the user is sleeping while the insulin infusion device is operating in the automatic mode; in response to determining that the user is sleeping, transition from the first target glucose setpoint value to a second target glucose setpoint value for use during the automatic mode, the transitioning occurring without user input, and the second target glucose setpoint value different than the first target glucose setpoint value; and continue to operate the insulin infusion device in the automatic mode to automatically control delivery of insulin to the user, in accordance with the second target glucose setpoint value.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
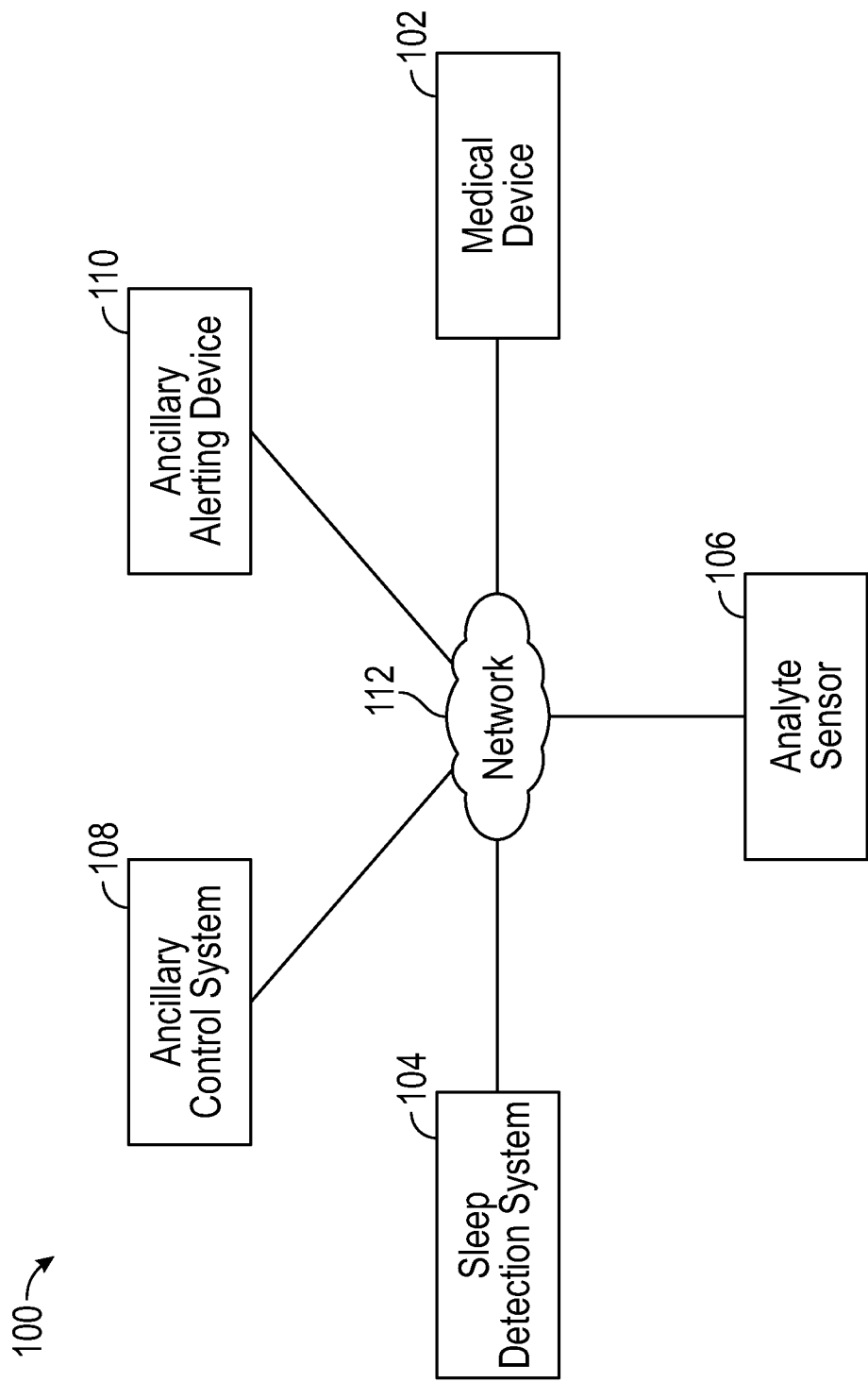
FIG. 1 is a simplified block diagram representation of an exemplary embodiment of a system that includes a medical device and a sleep detection system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be configurable to be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

Turning now to FIG. 1, exemplary embodiments of a system 100 include, without limitation: a medical device 102 that regulates delivery of medication to a user; and a sleep detection system 104 configured to generate user status data that indicates sleeping status of the user. The medical device 102 and the sleep detection system 104 are owned by, operated by, or otherwise associated with a user/patient. The output of the sleep detection system 104 can be used to influence features, functions, and/or therapy-related operations of the medical device 102. Certain embodiments of the system 100 may include any or all of the following, without limitation: an analyte sensor 106 to measure a physiological characteristic of the user, such that sensor data obtained from the analyte sensor 106 can be used to control, regulate, or otherwise influence the operation of the medical device 102; an ancillary control system 108 configured to remotely control at least some features, functions, or operations of the medical device 102 via suitably formatted commands, instructions, or control signals; and an ancillary alerting device 110 configured to generate alerts, alarms, messages, and/or notifications associated with the operation of the medical device 102. Additionally or alternatively, the ancillary alerting device 110 is configured to remotely control or regulate the generation or outputting/annunciation of such alerts, alarms, messages, and/or notifications by a component of the system 100 (e.g., the medical device 102 or another device that is capable of displaying, presenting, playing, transmitting, or otherwise outputting such alerts, alarms, message, and/or notifications). Other configurations and topologies for the system 100 are also contemplated here, such as a system that includes additional intermediary, interface, or data repeating devices in the data path between a sending device and a receiving device.

At least some of the components of the system 100 are communicatively coupled with one another to support data communication, signaling, and/or transmission of control commands as needed, via at least one communications network 112. The at least one communications network 112 may support wireless data communication and/or data communication using tangible data communication links. FIG. 1 depicts network communication links in a simplified manner. In practice, the system 100 may cooperate with and leverage any number of wireless and any number of wired data communication networks maintained or operated by various entities and providers. Accordingly, communication between the various components of the system 100 may involve multiple network links and different data communication protocols. In this regard, the network can include or cooperate with any of the following, without limitation: a local area network; a wide area network; the Internet; a personal area network; a near-field data communication link; a cellular communication network; a satellite communication network; a video services or television broadcasting network; a network onboard a vehicle; or the like. The components of the system 100 may be suitably configured to support a variety of wireless and wired data communication protocols, technologies, and techniques as needed for compatibility with the at least one communication network 112.

The analyte sensor 106 may communicate sensor data to the medical device 102 for use in regulating or controlling operation of the medical device 102. Alternatively or additionally, the analyte sensor 106 may communicate sensor data to one or more other components in the system 100. The sleep detection system 104 may communicate user status data (that indicates sleeping status of the user) directly to the medical device 102, which receives and processes the user status data in an appropriate manner for use in regulating or controlling certain functions of the medical device 102. Alternatively or additionally, the sleep detection system 104 may communicate user status data to the ancillary control system 108, such that the ancillary control system 108 can remotely regulate or control certain functions of the medical device 102. For example, the ancillary control system 108 can be configured to remotely control operation of the medical device in response to output provided by the sleep detection system 104. Alternatively or additionally, the sleep detection system 104 may communicate user status data to the ancillary alerting device 110 for use in regulating or controlling alerts generated by the ancillary alerting device 110 (where the alerts are related to or associated with the operation of the medical device, the analyte sensor 106, etc.). As mentioned previously, the ancillary control system 108 may communicate control signals, commands, or instructions to the medical device 102, to the ancillary alerting device 110, and/or other components of the system 100 to regulate or control settings, features, functions, and/or operations of those components.

In certain embodiments, the sleep detection system 104 and the medical device 102 are implemented as physically distinct and separate components, as depicted in FIG. 1. In such embodiments, the sleep detection system 104 is external to the medical device 102 and is realized as an ancillary component, relative to the medical device 102. In accordance with alternative embodiments, however, the medical device 102 and the sleep detection system 104 can be combined into a single hardware component or provided as a set of attached hardware devices. For example, the medical device 102 may include the sleep detection system 104 or integrate the functionality of the sleep detection system 104. Similarly, the ancillary control system 108 can be incorporated with the sleep detection system 104 or the ancillary alerting device 110 in some embodiments. Similarly, the ancillary alerting device 110 can be incorporated with the sleep detection system 104 in certain embodiments. These and other arrangements, deployments, and topologies of the system 100 are contemplated by this disclosure.

As described in more detail below, the sleep detection system 104 detects or determines whether the user is awake or sleeping. The sleep detection system 104 may also determine other sleep-related characteristics, such as the sleep onset time, the waking time, the duration of sleep, a quality metric or measurement that indicates how well the user slept, etc. The sleep detection system 104 generates and communicates user status data (that indicates the sleeping status of the user) to a destination device of the system 100, e.g., the medical device 102. In response to the sleeping status of the user, certain functions, settings, and/or operations of the medical device 102 can be regulated, controlled, or adjusted in an appropriate manner. In certain embodiments, a sleep mode alerting scheme of the medical device 102 is activated when the user is sleeping. The sleep mode alerting scheme regulates the generation, timing, prioritization, and/or output type of alerts associated with operation of the medical device 102. In accordance with certain embodiments where the medical device 102 is an insulin infusion device, a target glucose setpoint value is adjusted (e.g., lowered) when the sleep detection system 104 determines that the user is sleeping. The lowered target glucose setpoint value is utilized during an automatic insulin delivery mode while the user remains asleep.

Figure 2:
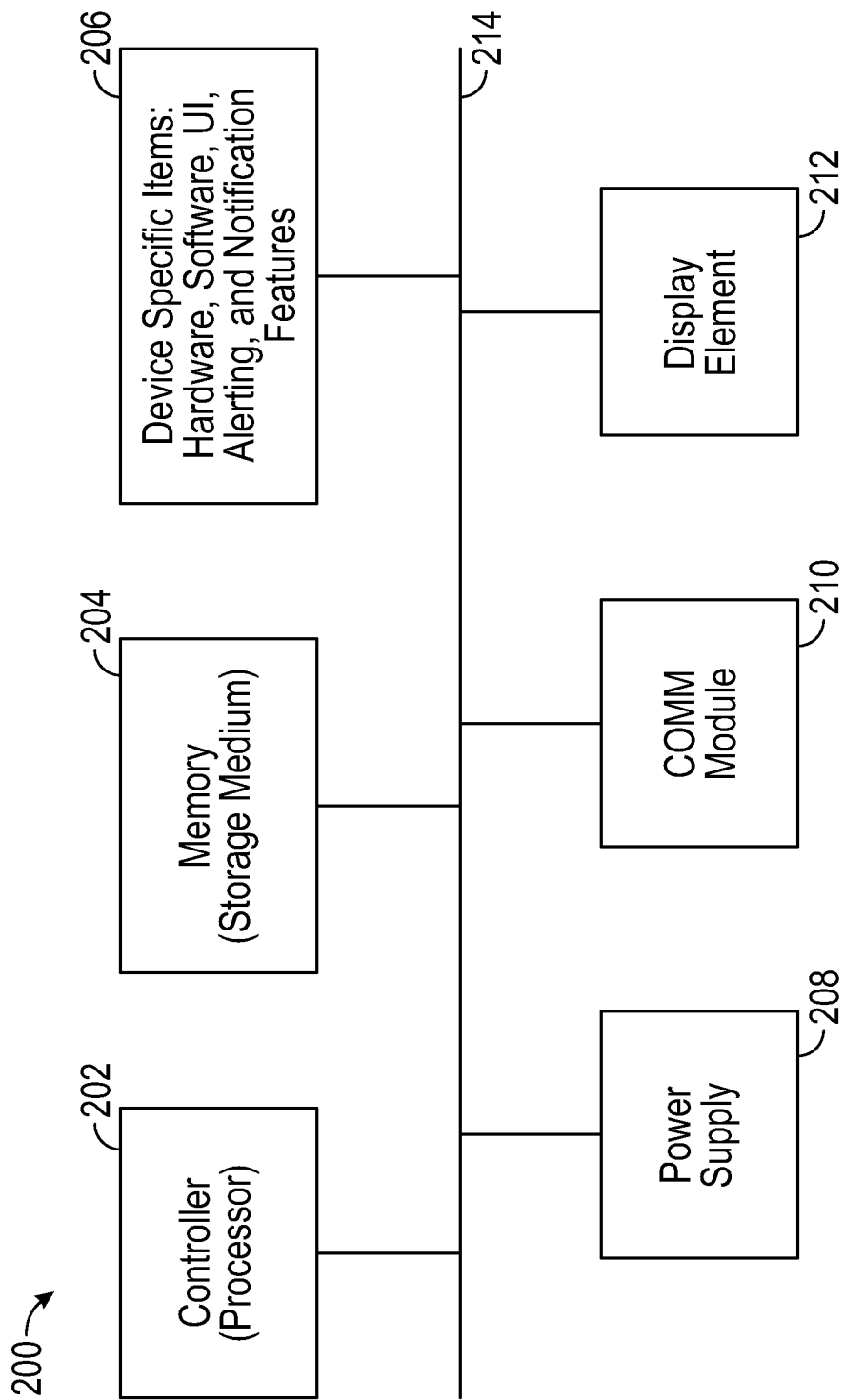
FIG. 2 is a block diagram representation of an exemplary embodiment of a computer-based or processor-based device suitable for deployment in the system shown in FIG. 1.

In accordance with certain embodiments, any or all of the components shown in FIG. 1 can be implemented as a computer-based or a processor-based device, system, or component having suitably configured hardware and software written to perform the functions and methods needed to support the features described herein. In this regard, FIG. 2 is a simplified block diagram representation of an exemplary embodiment of a computer-based or processor-based device 200 that is suitable for deployment in the system 100 shown in FIG. 1.

The illustrated embodiment of the device 200 is intended to be a high-level and generic representation of one suitable platform. In this regard, any computer-based or processor-based component of the system 100 can utilize the architecture of the device 200. The illustrated embodiment of the device 200 generally includes, without limitation: at least one controller (or processor) 202; a suitable amount of memory 204 that is associated with the at least one controller 202; device-specific items 206 (including, without limitation: hardware, software, firmware, user interface (UI), alerting, and notification features); a power supply 208 such as a disposable or rechargeable battery; a communication module 210; and a display element 212. Of course, an implementation of the device 200 may include additional elements, components, modules, and functionality configured to support various features that are unrelated to the primary subject matter described here. For example, the device 200 may include certain features and elements to support conventional functions that might be related to the particular implementation and deployment of the device 200 (e.g., haptic technology). In practice, the elements of the device 200 may be coupled together via at least one bus or any suitable interconnection architecture 214.

The at least one controller 202 may be implemented or performed with a general purpose processor, a content addressable memory, a microcontroller unit, a digital signal processor, an application specific integrated circuit, a field programmable gate array, any suitable programmable logic device, discrete gate or transistor logic, discrete hardware components, or any combination designed to perform the functions described here. Moreover, the at least one controller 202 may be implemented as a combination of computing devices, e.g., a combination of a digital signal processor and a microprocessor, a plurality of microprocessors, one or more microprocessors in conjunction with a digital signal processor core, or any other such configuration.

The memory 204 may be realized as at least one memory element, device, module, or unit, such as: RAM memory, flash memory, EPROM memory, EEPROM memory, registers, a hard disk, a removable disk, a CD-ROM, or any other form of storage medium known in the art. In this regard, the memory 204 can be coupled to the at least one controller 202 such that the at least one controller 202 can read information from, and write information to, the memory 204. In the alternative, the memory 204 may be integral to the at least one controller 202. As an example, the at least one controller 202 and the memory 204 may reside in an ASIC. At least a portion of the memory 204 can be realized as a computer storage medium that is operatively associated with the at least one controller 202, e.g., a tangible, non-transitory computer-readable medium having computer-executable instructions stored thereon. The computer-executable instructions are configurable to be executed by the at least one controller 202 to cause the at least one controller 202 to perform certain tasks, operations, functions, and processes that are specific to the particular embodiment. In this regard, the memory 204 may represent one suitable implementation of such computer-readable media. Alternatively or additionally, the device 200 could receive and cooperate with computer-readable media (not separately shown) that is realized as a portable or mobile component or platform, e.g., a portable hard drive, a USB flash drive, an optical disc, or the like.

The device-specific items 206 may vary from one embodiment of the device 200 to another. For example, the device-specific items 206 will support: sensor device operations when the device 200 is realized as a sensor device; smartphone features and functionality when the device 200 is realized as a smartphone; activity tracker features and functionality when the device 200 is realized as an activity tracker; smart watch features and functionality when the device 200 is realized as a smart watch; medical device features and functionality when the device is realized as a medical device; etc. In practice, certain portions or aspects of the device-specific items 206 may be implemented in one or more of the other blocks depicted in FIG. 2.

If present, the UI of the device 200 may include or cooperate with various features to allow a user to interact with the device 200. Accordingly, the UI may include various human-to-machine interfaces, e.g., a keypad, keys, a keyboard, buttons, switches, knobs, a touchpad, a joystick, a pointing device, a virtual writing tablet, a touch screen, a microphone, or any device, component, or function that enables the user to select options, input information, or otherwise control the operation of the device 200. The UI may include one or more graphical user interface (GUI) control elements that enable a user to manipulate or otherwise interact with an application via the display element 212. The display element 212 and/or the device-specific items 206 may be utilized to generate, present, render, output, and/or annunciate alerts, alarms, messages, or notifications that are associated with operation of the medical device 102, associated with a status or condition of the user, associated with operation, status, or condition of the system 100, etc.

The communication module 210 facilitates data communication between the device 200 and other components as needed during the operation of the device 200. In the context of this description, the communication module 210 can be employed to transmit or stream device-related control data, patient-related user status (e.g., sleeping status data), device-related status or operational data, sensor data, calibration data, and the like. It should be appreciated that the particular configuration and functionality of the communication module 210 can vary depending on the hardware platform and specific implementation of the device 200. In practice, an embodiment of the device 200 may support wireless data communication and/or wired data communication, using various data communication protocols. For example, the communication module 210 could support one or more wireless data communication protocols, techniques, or methodologies, including, without limitation: RF; IrDA (infrared); Bluetooth; BLE; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB. Moreover, the communication module 210 could support one or more wired/cabled data communication protocols, including, without limitation: Ethernet; powerline; home network communication protocols; USB; IEEE 1394 (Firewire); hospital network communication protocols; and proprietary data communication protocols.

The display element 212 is suitably configured to enable the device 200 to render and display various screens, recommendation messages, alerts, alarms, notifications, GUIs, GUI control elements, drop down menus, auto-fill fields, text entry fields, message fields, or the like. Of course, the display element 212 may also be utilized for the display of other information during the operation of the device 200, as is well understood. Notably, the specific configuration, operating characteristics, size, resolution, and functionality of the display element 212 can vary depending upon the implementation of the device 200.

As shown in FIG. 1, the system 100 can support any type of medical device 102 that is compatible with the features and functionality described here. In certain embodiments, however, the medical device 102 includes or is realized as an insulin infusion device, e.g., a portable patient-worn or patient-carried insulin pump. For the sake of brevity, conventional techniques related to insulin infusion device operation, infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Generally, a fluid infusion device includes a fluid pump mechanism having a motor or other actuation arrangement that is operable to linearly displace a plunger (or stopper) of a fluid reservoir provided within the fluid infusion device to deliver a dosage of fluid medication, such as insulin, to the body of a user. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For a glucose control system suitable for use by diabetic patients, a closed-loop or automatic operating mode can be used to generate insulin dosage commands based on a difference between a current (or most recent) measurement of the interstitial fluid glucose level in the body of the user and a target (or reference) glucose setpoint value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

Figure 3:
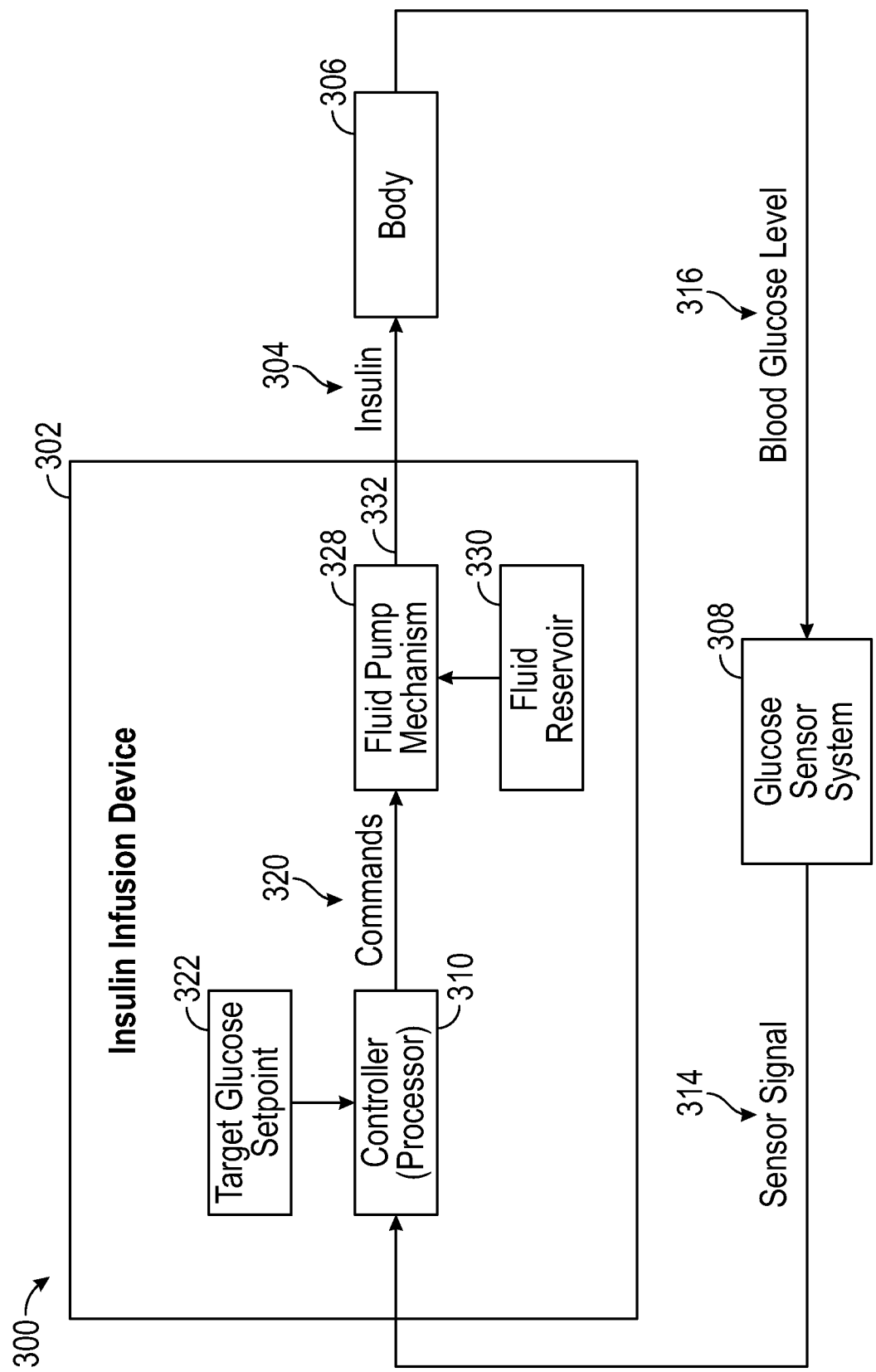
FIG. 3 is a block diagram representation of a closed loop glucose control system arranged in accordance with certain embodiments.

As mentioned above, the medical device 102 is suitably configured and programmed to support an automatic mode to automatically control delivery of insulin to the user. In this regard, FIG. 3 is a simplified block diagram representation of a closed loop glucose control system 300 arranged in accordance with certain embodiments. The system 300 depicted in FIG. 3 functions to regulate the rate of fluid infusion into a body of a user based on feedback from an analyte concentration measurement taken from the body. In particular embodiments, the system 300 is implemented as an automated control system for regulating the rate of insulin infusion into the body of a user based on a glucose concentration measurement taken from the body. The system 300 is designed to model the physiological response of the user to control an insulin infusion device 302 in an appropriate manner to release insulin 304 into the body 306 of the user in a similar concentration profile as would be created by fully functioning human β-cells when responding to changes in blood glucose concentrations in the body. Thus, the system 300 simulates the body's natural insulin response to blood glucose levels and not only makes efficient use of insulin, but also accounts for other bodily functions as well since insulin has both metabolic and mitogenic effects.

Certain embodiments of the system 300 include, without limitation: the insulin infusion device 302; a glucose sensor system 308 (e.g., the analyte sensor 106 shown in FIG. 1); and at least one controller 310, which may be incorporated in the insulin infusion device 302 as shown in FIG. 3. The glucose sensor system 308 generates a sensor signal 314 representative of blood glucose levels 316 in the body 306, and provides the sensor signal 314 to the at least one controller 310. The at least one controller 310 receives the sensor signal 314 and generates commands 320 that regulate the timing and dosage of insulin 304 delivered by the insulin infusion device 302. The commands 320 are generated in response to various factors, variables, settings, and control algorithms utilized by the insulin infusion device 302. For example, the commands 320 (and, therefore, the delivery of insulin 304) can be influenced by a variable target glucose setpoint value 322 that is maintained and regulated by the insulin infusion device 302. As described in more detail below, the target glucose setpoint value 322 can be lowered when the system 100 (see FIG. 1) determines that the user is asleep, and can be raised when the system 100 determines that the user is no longer asleep.

Generally, the glucose sensor system 308 includes a continuous glucose sensor, sensor electrical components to provide power to the sensor and generate the sensor signal 314, a sensor communication system to carry the sensor signal 314 to the at least one controller 310, and a sensor system housing for the electrical components and the sensor communication system. As mentioned above with reference to FIG. 2, the glucose sensor system 308 may be implemented as a computer-based or processor-based component having the described configuration and features.

Typically, the at least one controller 310 includes controller electrical components and software to generate commands for the insulin infusion device 302 based on the sensor signal 314, the target glucose setpoint value 322, and other user-specific parameters, settings, and factors. The at least one controller 310 may include a controller communication system to receive the sensor signal 314 and issue the commands 320.

Generally, the insulin infusion device 302 includes a fluid pump mechanism 328, a fluid reservoir 330 for the medication (e.g., insulin), and an infusion tube 332 to infuse the insulin 304 into the body 306. In certain embodiments, the insulin infusion device 302 includes an infusion communication system to handle the commands 320 from the at least one controller 310, electrical components and programmed logic to activate the fluid pump mechanism 328 motor according to the commands 320, and a housing to hold the components of the insulin infusion device 302. Accordingly, the fluid pump mechanism 328 receives the commands 320 and delivers the insulin 304 from the fluid reservoir 330 to the body 306 in accordance with the commands 320. It should be appreciated that an embodiment of the insulin infusion device 302 can include additional elements, components, and features that may provide conventional functionality that need not be described herein. Moreover, an embodiment of the insulin infusion device 302 can include alternative elements, components, and features if so desired, as long as the intended and described functionality remains in place. In this regard, as mentioned above with reference to FIG. 2, the insulin infusion device 302 may be implemented as a computer-based or processor-based components having the described configuration and features, including the display element 212 or other device-specific items 206 as described above.

The at least one controller 310 is configured and programmed to regulate the operation of the fluid pump mechanism 328 and other functions of the insulin infusion device 302. The at least one controller 310 controls the fluid pump mechanism 328 to deliver the fluid medication (e.g., insulin) from the fluid reservoir 330 to the body 306. As mentioned above, the at least one controller 310 can be housed in the infusion device housing, wherein the infusion communication system is an electrical trace or a wire that carries the commands 320 from the at least one controller 310 to the fluid pump mechanism 328. In alternative embodiments, the at least one controller 310 can be housed in the sensor system housing, wherein the sensor communication system is an electrical trace or a wire that carries the sensor signal 314 from the sensor electrical components to the at least one controller 310. In accordance with some embodiments, the at least one controller 310 has its own housing or is included in a supplemental or ancillary device. In other embodiments, the at least one controller 310, the insulin infusion device 302, and the glucose sensor system 308 are all located within one common housing.

The sleep detection system 104 employs at least one sensor to obtain corresponding user-specific sensor data (i.e., user status data). The obtained user status data is processed or analyzed by the sleep detection system 104 and/or by a suitably configured device or component of the system 100 to determine whether the user is sleeping. The obtained user status data may also be processed or analyzed to obtain certain sleep-related parameters, characteristics, and/or metadata for the user. For example, the obtained user status data may identify, include, or indicate any or all of the following, without limitation: timestamp data corresponding to when the user initially fell asleep; timestamp data corresponding to when the user wakes up; timestamp data corresponding to periods of restless sleep; a sleep quality metric for the user, which indicates how well the user slept for a given period of time; a sleep duration metric for the user, which indicates how long the user continuously slept; user posture or position information, which indicates orientation of the user's body during sleep; body temperature; heartrate; blood pressure; respiratory rate; sweat level; eye or eyelid movement, which may indicate periods of rapid eye movement sleep; eyelid position (e.g., open or closed); images or video of the user; etc.

The sleep detection system 104 may include, cooperate with, or be implemented as a gesture-based system, a motion-based system, an activity-based system, a heartrate-based system, or the like. In certain embodiments, the sleep detection system 104 may be realized as a unitary "self-contained" wearable system that communicates with one or more other components of the system 100. For example, the sleep detection system 104 can be implemented with a wearable device such as an activity monitor device, a smart watch device, a smart bracelet device, or the like. In some embodiments, the sleep detection system 104 may be realized as a portable or wearable device that includes or communicates with one or more external or ancillary sensor devices, units, or components. For example, the sleep detection system 104 can be implemented with a wearable or portable smart device that is linked with one or more external sensors worn or carried by the user. These and other possible deployments of the sleep detection system 104 are contemplated by this disclosure. In this regard, United States patent publication number US 2020/0135320 and U.S. patent application Ser. No. 16/886,360 (filed May 28, 2020) disclose gesture-based physical behavior detection systems that are suitable for use as the sleep detection system 104; the entire content of these United States patent documents is incorporated by reference herein.

Figure 4:
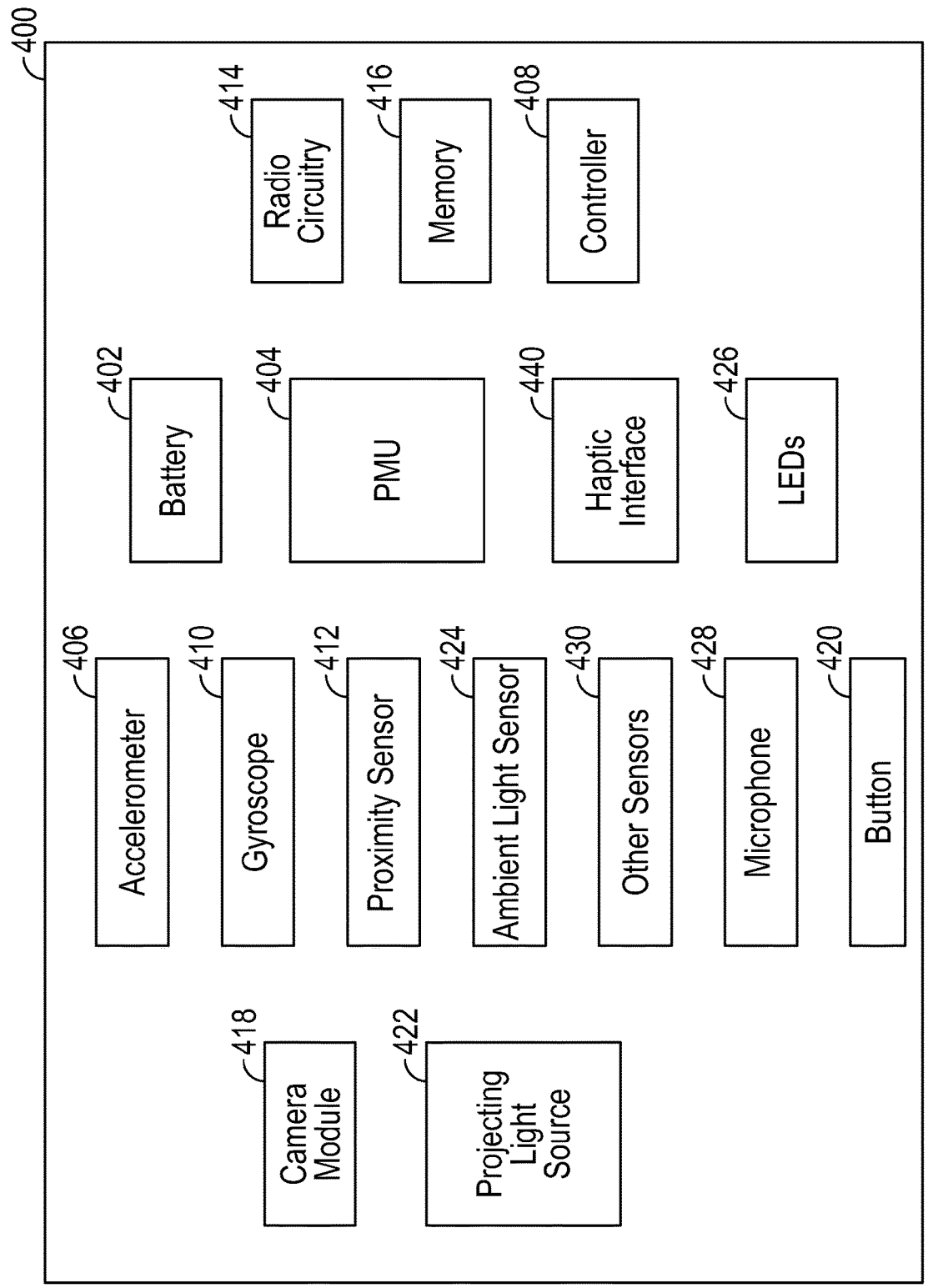
FIG. 4 is a block diagram representation of a sleep detection system arranged in accordance with certain embodiments.

FIG. 4 is a block diagram representation of a sleep detection system 400 arranged in accordance with certain embodiments. The sleep detection system 400 is suitable for use with the system 100 shown FIG. 1. In certain embodiments, the sleep detection system 400 is deployed as a wearable electronic device in the form factor of a bracelet or wristband that is worn around the wrist or arm of a user's dominant hand. The sleep detection system 400 may optionally be implemented using a modular design, wherein individual modules include one or more subsets of the disclosed components and overall functionality. The user may choose to add specific modules based on personal preferences and requirements.

The sleep detection system 400 includes a battery 402 and a power management unit (PMU) 404 to deliver power at the proper supply voltage levels to all electronic circuits and components. The PMU 404 may also include battery-recharging circuitry. The PMU 404 may also include hardware, such as switches, that allows power to specific electronics circuits and components to be cut off when not in use.

When there is no movement-based or gesture-based behavior event in progress, most circuitry and components in the sleep detection system 400 are switched off to conserve power. Only circuitry and components that are required to detect or help predict the start of a behavior event of interest (such as sleeping or waking) may remain enabled. For example, if no motion is being detected, all sensor circuits but an accelerometer 406 may be switched off and the accelerometer 406 may be put in a low-power wake-on-motion mode or in another lower power mode that consumes less power and uses less processing resources than its high performance active mode. A controller 408 of the sleep detection system 400 may also be placed into a low-power mode to conserve power. When motion or a certain motion pattern is detected, the accelerometer 406 and/or the controller 408 may switch into a higher power mode and additional sensors such as, for example, a gyroscope 410 and/or a proximity sensor 412 may also be enabled. When a potential start of a movement-based or gesture-based event is detected, memory variables for storing event-specific parameters, such as gesture types, gesture duration, etc. can be initialized.

In another example, upon detection of user motion, the accelerometer 406 switches into a higher power mode, but other sensors remain switched off until the data from the accelerometer 406 indicates that the start of a behavior event has likely occurred. At that point in time, additional sensors such as the gyroscope 410 and the proximity sensor 412 may be enabled.

In another example, when there is no behavior event in progress, both the accelerometer 406 and gyroscope 410 are enabled but at least one of either the accelerometer 406 or the gyroscope 410 is placed in a lower power mode compared to their regular power mode. For example, the sampling rate may be reduced to conserve power. Similarly, the circuitry required to transfer data from the sleep detection system 400 to a destination device may be placed in a lower power mode. For example, radio circuitry 414 could be disabled. Similarly, the circuitry required to transfer data from the sleep detection system 400 may be placed in a lower power mode. For example, the radio circuitry 414 could be disabled until a possible or likely start of a behavior event has been determined. Alternatively, it may remain enabled but in a low power state to maintain the connection between the sleep detection system 400 and one or more other components of the system 100, but without transferring user status data, sensor data, or the like.

In yet another example, all motion-detection related circuitry may be switched off if, based on certain metadata, it is determined that the occurrence of a particular behavior event, such as a food intake event, is unlikely. This may be desirable to further conserve power. Metadata used to make this determination may, among other things, include one or more of the following: time of the day, location, ambient light levels, proximity sensing, and detection that the sleep detection system 400 has been removed from the wrist or hand, detection that the sleep detection system 400 is being charged, or the like. Metadata may be generated and collected by the sleep detection system 400. Alternatively, metadata may be collected by another device that is external to the sleep detection system 400 and is configured to directly or indirectly exchange information with the sleep detection system 400. It is also possible that some metadata is generated and collected by the sleep detection system 400, while other metadata is generated and collected by a device that is external to the sleep detection system 400. In case some or all of the metadata is generated and collected external to the sleep detection system 400, the sleep detection system 400 may periodically or from time to time power up its radio circuitry 414 to retrieve metadata related information from another device.

In certain embodiments, some or all of the sensors may be turned on or placed in a higher power mode if certain metadata indicates that the occurrence of a particular behavior event, such as the user falling asleep, is likely. Metadata used to make this determination may, among other things, include one or more of the following: time of the day; location; ambient light levels; proximity sensing; historical user behavior patterns. Some or all of the metadata may be collected by sleep detection system 400 or by an ancillary device that cooperates or communicates with the sleep detection system 400, as mentioned above.

User status data used to track certain aspects of a user's behavior may be stored locally inside memory 416 of the sleep detection system 400 and processed locally using the controller 408 of the sleep detection system 400. User status data may also be transferred to the medical device 102, the ancillary control system 108, and/or the ancillary alerting device 110 (using, for example, the radio circuitry 414) for further processing and analysis. It is also possible that some of the processing and analysis are performed locally by the sleep detection system 400, while further processing and analysis are performed by one or more other components of the system 100.

The detection of the start of a behavior event, such as the start of a sleeping period, may trigger the power up and/or activation of additional sensors and circuitry, such as a camera module 418. Power up and/or activation of additional sensors and circuitry may occur at the same time as the detection of the behavior event of interest or some time thereafter. Specific sensors and circuitry may be turned on only at specific times during a detected event, and may be switched off otherwise to conserve power. It is also possible that the camera module 418 only gets powered up or activated upon explicit user intervention such as, for example, pushing and holding a button 420. Releasing the button 420 may turn off the camera module 418 to conserve power.

When the camera module 418 is powered up, a projecting light source 422 may also be enabled to provide visual feedback to the user about the area that is within view of the camera or to otherwise illuminate the field of view. Alternatively, the projecting light source 422 may only be activated sometime after the camera module 418 has been activated. In certain cases, additional conditions may need to be met before the projecting light source 422 is activated. Such conditions may include: the determination that the projecting light source 422 is likely aiming in the direction of the object of interest; the determination that the sleep detection system 400 is not moving excessively; or the like. In some embodiments, one or more light emitting diodes (LEDs) 426 may be used as the projecting light source 422.

Images may be tagged with additional information or metadata such as: camera focal information; proximity information from the proximity sensor 412; ambient light levels information from an ambient light sensor 424; timestamp information; etc. Such additional information or metadata may be used during the processing and analysis of the user status data.

The projecting light source 422 may also be used to communicate other information. As an example, an ancillary device may use inputs from one or more proximity sensors 412, process those inputs to determine if the camera module 418 is within the proper distance range from the object of interest, and use one or more light sources to communicate that the camera is within the proper distance range, that the user needs to increase the distance between camera and the object of interest, or that the user needs to reduce the distance between the camera and the object of interest.

The projecting light source 422 may also be used in combination with the ambient light sensor 424 to communicate to the user if the ambient light is insufficient or too strong for an adequate quality image capture. The projecting light source 422 may also be used to communicate information including, but not limited to, a low battery situation or a functional defect.

The projecting light source 422 may also be used to communicate dietary coaching information. As an example, the projecting light source 422 might, among other things, indicate if not enough or too much time has expired since a previous food intake event, or may communicate to the user how he/she is doing against specific dietary goals.

Signaling mechanisms to convey specific messages using one or more projecting light sources 422 may include, but are not limited to, one or more of the following: specific light intensities or light intensity patterns; specific light colors or light color patterns; specific spatial or temporal light patterns. Multiple mechanisms may also be combined to signal one specific message.

A microphone 428 may be used by the user to add specific or custom labels or messages to a detected event and/or image. Audio snippets may be processed by a voice recognition engine.

In certain embodiments, the accelerometer 406 (possibly combined with other sensors, including other inertial sensors) may, in addition to tracking at least one parameter that is directly related to a gesture-based behavior event, also be used to track one or more parameters that are not directly related to that particular event. Such parameters may, among other things, include physical activity, sleep, eating, or stress.

In addition to the particular sensors, detectors, and components mentioned above, the sleep detection system 400 may include or cooperate with any number of other sensors 430 as appropriate for the particular embodiment. The sleep detection system 400 obtains user status data from one or more of its sensors, detectors, and sources, wherein the user status data indicates sleeping status of the user. The user status data can be analyzed and processed by the sleep detection system 400 (and/or by one or more other components of the system 100) to determine whether the user is sleeping and, in certain embodiments, to determine additional information, characteristics, or metrics related to the user's sleeping status. In certain embodiments, the sleep detection system 400 and/or an ancillary system or device determines the user's sleeping status primarily based on the output of user-worn motion sensors, movement sensors, one or more inertial sensors (e.g., one or more accelerometers and/or one or more gyroscopes), one or more GPS sensors, one or more magnetometers, one or more force or physical pressure sensors, or the like, which are suitably configured, positioned, and arranged to measure physical movement or motion of the user's limbs, digits, joints, facial features, head, and/or other body parts.

In some embodiments, the sleep detection system 400 includes at least one haptic interface 440 that is suitably configured and operated to provide haptic feedback as an output. The at least one haptic interface 440 generates output(s) that can be experienced by the sense of touch by the user, e.g., mechanical force, vibration, movement, temperature changes, or the like. Haptic feedback generated by the at least one haptic interface 440 may represent or be associated with one or more of the following, without limitation: reminders; alerts; confirmations; notifications; messages; numerical values (such as measurements); status indicators; or any other type of output provided by the sleep detection system 400.

In certain embodiments, the user status data (e.g., sensor data) is provided to a gesture recognizer unit or processing module. To this end, sensor data may be sent in raw format. Alternatively, a source of sensor data may perform some processing (e.g., filtering, compression, or formatting) on raw sensor data before sending the processed sensor data to the gesture recognizer unit. The gesture recognizer unit analyzes the incoming sensor data and converts the incoming sensor data into a stream of corresponding gestures, which may be predetermined or otherwise classified or categorized. The gesture recognizer unit may use one or more ancillary inputs to aid in the gesture determination process. Nonlimiting examples of an ancillary input include: time of day; the probability of a specific gesture occurring based on statistical analysis of historical gesture data for that user; geographical location; heart rate; other physiological sensor inputs. Other ancillary inputs are also possible.

The output of the gesture recognizer unit—the detected gestures—can be sent to an event detector or processing module. The event detector analyzes the incoming stream of gestures to determine if the start of an event of interest (e.g., sleep) has occurred, whether an event is ongoing, whether an event has ended, or the like. For example, if the event detector is implemented as a sleep detector intended to capture sleeping/waking events, it will be suitably configured to determine if the start of a sleeping period has occurred, if the user is still sleeping, or if the user is awake. Although this description focuses on sleep detection, a gesture-based physical behavior detection system may be suitably configured to monitor other types of physical behavior or activities. Such activities include, without limitation: reading; drinking; smoking; getting dressed; turning down a bed; making a bed; brushing teeth; combing hair; talking on the phone; inhaling or injecting a medication; and activities related to hand hygiene or personal hygiene.

Referring again to FIG. 1, certain functions, features, and/or therapy related operations of the medical device 102 can be adjusted or modified in response to the output of the sleep detection system 104. More specifically, operation of the medical device 102 can be controlled or regulated based on a determination that the user is sleeping. For example, if the system 100 determines that the user is sleeping, a sleep mode alerting scheme of the medical device 102 can be activated (instead of a default alerting scheme). As another example, if the system 100 determines that the user is sleeping, then a target glucose setpoint value (utilized by an insulin infusion device during an automatic insulin delivery mode) can be temporarily lowered.

Figure 5:
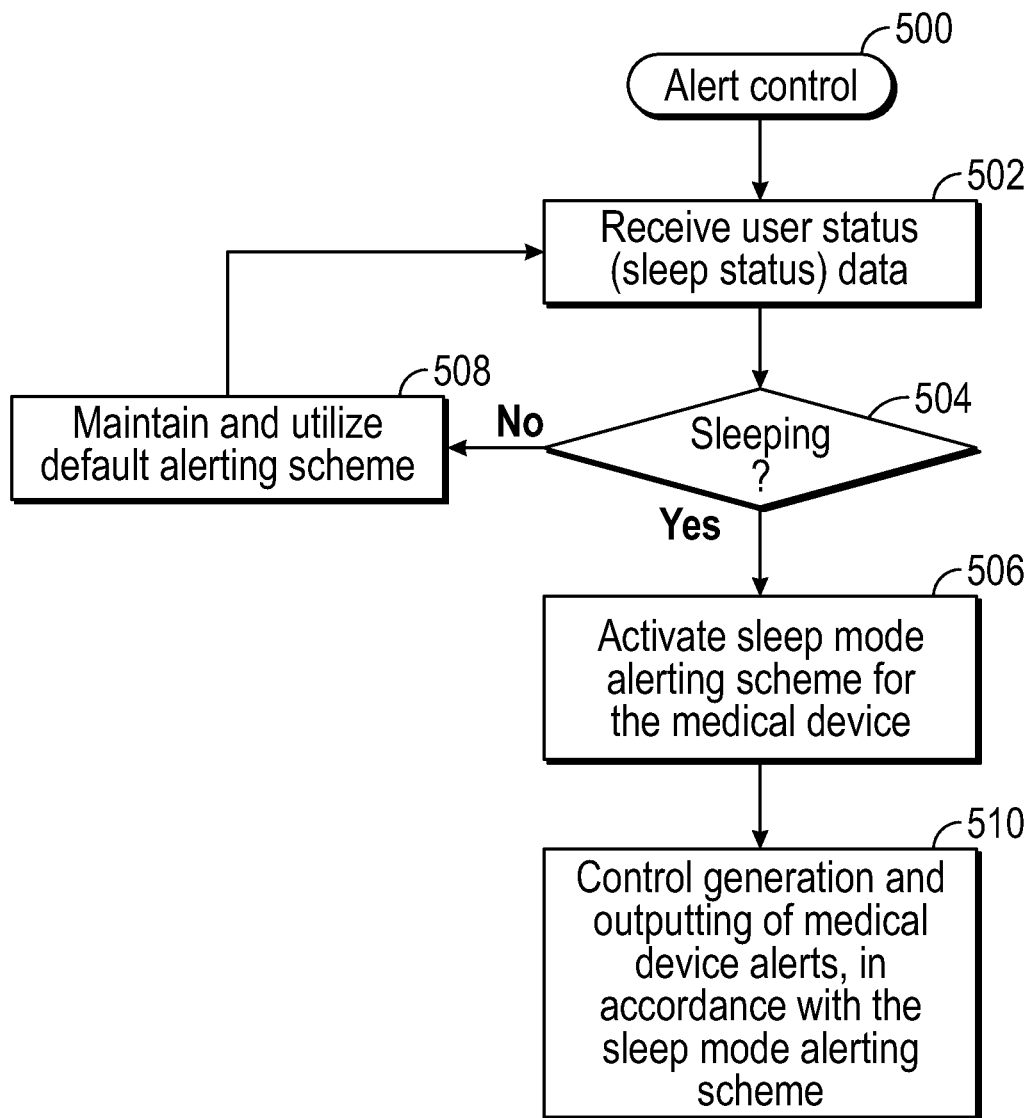
FIG. 5 is a flow chart that illustrates an alert control process according to certain embodiments.

FIG. 5 is a flow chart that illustrates an alert control process 500 according to certain embodiments. The process 500 represents an automated method of controlling alerts associated with the operation of a medical device, such as an insulin infusion device. The process 500 receives user status data (e.g., sleep status data) that indicates the sleeping status of a user of the medical device (task 502). As mentioned above, the user status data is generated by sensors, detector units, or other sources of data that are included with or associated with a suitably configured sleep detection system (e.g., the analyte sensor 106, the accelerometer 406, the gyroscope 410, the proximity sensor 412, one or more other sensors 430, the microphone 428, and/or the camera module 418). Depending on the particular embodiment, task 502 may be performed by the sleep detection system and/or by an ancillary system or device other than the sleep detection system. The process 500 continues by analyzing or processing at least some of the received user status data to determine whether the user is sleeping (query task 504). If analysis of the user status data indicates that the user is sleeping (the "Yes" branch of query task 504), then the process 500 activates a sleep mode alerting scheme for the medical device (task 506). The sleep mode alerting scheme replaces, supplements, or modifies the existing alerting scheme (which may be a default, baseline, or standard alerting scheme utilized by the medical device, i.e., an unmodified scheme that is utilized during normally expected operation of the medical device while the user is awake). If analysis of the user status data indicates that the user is not asleep (the "No" branch of query task 504), then the process maintains and utilizes the currently active alerting scheme of the medical device, e.g., the default, baseline, or standard alerting scheme (task 508). After activating the sleep mode alerting scheme, the process 500 continues by controlling the generation and outputting of alerts associated with the operation of the medical device (task 510), wherein the generation and outputting of alerts are performed in accordance with the activated sleep mode alerting scheme.

In certain embodiments, the sleep mode alerting scheme silences (e.g., inhibits the generation or outputting, or generates but mutes), temporarily disables, or delays the outputting of at least one alert while the user is asleep. The sleep mode alerting scheme may queue at least one alert for subsequent presentation or outputting to the user in a first-in, first-out order or a rearranged order that may be influenced by a priority assigned to the alerts, the importance of the alerts, or any other criteria. In this regard, the process 500 can delay or queue an alert such that it does not wake up the user, but is displayed, output, or otherwise presented after the user wakes up. The user can be notified of any delayed or queued alerts, and reminded or prompted to view and clear such alerts. Delayed or queued alerts may be identified in a selectable list that allows the user to choose which alerts to view, and in which order. The user may be required to view and clear some alerts to silence an ongoing alert or to prevent repeated notifications or reminders. In some embodiments, delayed or queued alerts may be displayed in one or more windows or in one or more messages in succession or concurrently, and displayed messages/windows may be accompanied by audible alert sounds and/or haptic feedback intended to notify the user or otherwise obtain the attention of the user. It should be appreciated that the specific manner in which delayed, silenced, or queued alerts/messages are subsequently presented to the user may vary, depending on the particular implementation, the intended application of the medical device, user preferences or settings, healthcare provider preferences or settings, or the like.

In accordance with some embodiments, the sleep mode alerting scheme changes a default output type, mode, or source (for at least one alert) to an elevated output type, mode, or source that is more aggressive than the default output type, for example, an output type that is unmodified, unrestricted, or is normally utilized by the device during waking hours. As used here, an alert that is "more aggressive" than its default counterpart is louder, more noticeable, more recognizable, more frequent or repetitive, stronger, or otherwise designed to wake up a sleeping user. For example, the default output type may be associated with outputting of an alert by a default alerting device, such as the medical device itself. In contrast, the elevated output type may be associated with outputting of an alert by an ancillary alerting device that is different than the default alerting device, such as an alarm clock, the user's mobile phone, a security system alarm unit, the user's smart-watch, or the like. Different annunciation/output types include, without limitation: audible alarms, alerts, or messages; haptic feedback, such as vibration of a device in the system; visible alarms, alerts, or messages, such as flashing lights, a pattern of lights, or illumination of a display screen; and displayable alarms, alerts, or messages. In certain embodiments, the elevated output type can be utilized in concert with, or in lieu of, the default output type. Accordingly, the sleep mode alerting scheme can utilize the elevated output types, modes, or sources for important, critical, time sensitive, and/or safety-related alerts that occur when the user is sleeping.

The medical device 102 can generate any number of alerts, notifications, messages, reminders, or the like (collectively referred to herein as "alerts"). The alerts can be ranked or prioritized in the context of the default alerting scheme and/or in the context of the sleep mode alerting scheme. At least some alerts can be reprioritized for the sleep mode alerting scheme. Alerts may be related to status of the medical device 102 (e.g., battery status), status of disposables or consumables used by the medical device 102 (e.g., insulin reservoir level), user/patient status, therapy delivery, calendar entries, or the like. Alerts can be prioritized based on their relationship or association with patient safety, operating health of the medical device 102, or the like. For example, routine reminders or notifications that are unrelated to therapy or patient health might be deemed "low priority" and, therefore, silenced while the user is sleeping. As another example, important or urgent alerts that relate to patient safety or critical functions or the medical device 102 may be deemed "high priority" and, therefore, kept active while the user is sleeping.

In some embodiments, the user status data provided by the sleep detection system 104 includes a sleep quality metric that measures, quantifies, or otherwise indicates how well the user has slept or how well the user is sleeping. For example, the sleep quality metric may be based on any or all of the following data, without limitation: heart rate; respiratory rate; amount of movement (tossing and turning) during sleep; eye movement; snoring sounds; etc. The sleep quality metric generated by the sleep detection system 104 can be used to regulate or adjust the sleep mode alerting scheme. More specifically, the sleep mode alerting scheme can be designed such that it regulates the generation or outputting of alerts as a function of the sleep quality metric generated by the sleep detection system. Thus, if the sleep quality metric indicates that the user has been sleeping well (e.g., in deep sleep or REM sleep), then the sleep mode alerting scheme can be adjusted to accommodate that sleeping state. If the sleep quality metric indicates that the user has not been sleeping well or is in a state of shallow or gentle sleep, then the sleep mode alerting scheme can be adjusted in a manner that assumes that the user is not actually sleeping, yet not fully awake. Accordingly, the manner in which different alerts are handled (e.g., silenced, delayed, deleted, queued, repeated) and/or the manner in which different alerts are annunciated or output (e.g., using the native functionality of the medical device 102, using an escalated or elevated output scheme, and/or using one or more ancillary alerting devices 110) can vary in response to the current value of the sleep quality metric.

In some embodiments, the user status data provided by the sleep detection system 104 includes a sleep duration metric that measures, quantifies, or otherwise indicates how long the user slept or how long the user has been sleeping. For example, the sleep duration metric may be a time value based on when the sleep detection system 104 determined that the user fell asleep. The sleep duration metric generated by the sleep detection system 104 can be used to regulate or adjust the sleep mode alerting scheme. More specifically, the sleep mode alerting scheme can be designed such that it regulates the generation or outputting of alerts as a function of the sleep duration metric generated by the sleep detection system. Thus, if the sleep duration metric indicates that the user has been continuously sleeping for an extended period of time (e.g., more than two hours), then the sleep mode alerting scheme can be adjusted to accommodate that sleeping state. If the sleep duration metric indicates that the user has only been sleeping for a few minutes, then the sleep mode alerting scheme can be adjusted in a manner that assumes that the user is not actually sleeping, yet not fully awake. Accordingly, the manner in which different alerts are handled (e.g., silenced, delayed, deleted, queued, repeated) and/or the manner in which different alerts are annunciated/output (e.g., using the native functionality of the medical device 102, using an escalated or elevated output scheme, and/or using one or more ancillary alerting devices 110) can vary in response to the current value of the sleep duration metric.

As one non-limiting example, a "Low Glucose" alert can be elevated to a higher priority during sleep. Moreover, the output characteristics of a "Low Glucose" alert can change in a dynamic manner if the user does not respond during sleep. As another non-limiting example, an "Occlusion" alarm (which may be utilized by a fluid infusion system) can be elevated to a higher priority during sleep, and its output characteristics can escalate in a dynamic manner if the user does not respond during sleep. As another non-limiting example, a "Low Reservoir" alert can be suppressed or given a lower priority during sleeping periods if the remaining operating time (or amount of fluid remaining in the reservoir) allows the alert to be addressed after the user's regular wake-up time. As another non-limiting example, a "Low Battery" alert can be suppressed, delayed, or given a lower priority during sleeping periods if the remaining battery time allows the alert to be addressed after the user wakes up. As another non-limiting example, a "High Glucose" alert can remain unchanged (i.e., its priority is not changed and its output characteristics remain the same) during periods of sleep.

Figure 6:
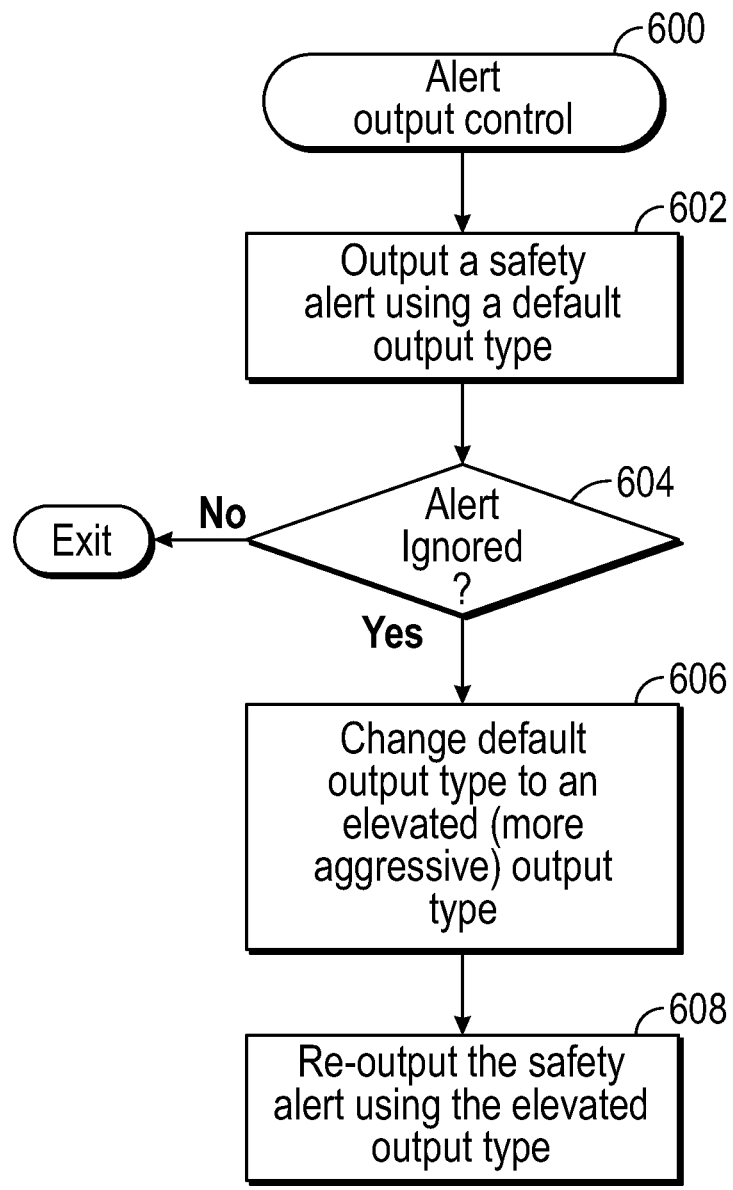
FIG. 6 is a flow chart that illustrates an alert annunciation/output control process according to certain embodiments.

FIG. 6 is a flow chart that illustrates an alert annunciation/output control process 600 according to certain embodiments. The process 600 may be performed in conjunction with the process 500 described above. Indeed, this description assumes that the process 600 is performed after the system 100 has determined that the user is sleeping. The process 600 outputs a safety alert using a default output type (task 602), and checks whether the safety alert has been ignored or attended to (query task 604). As used here, a safety alert is any alert that relates to, indicates, or is otherwise associated with a condition, a device state, user status, system state, or environmental condition that implicates the health, well-being, quality of life, or security of the user. In this regard, safety alerts can be distinguished from non-critical alerts, routine reminders, and unimportant messages that have little to no impact on patient health or therapy outcomes and, therefore, can be safely and confidently delayed, ignored, deleted, or disregarded during periods of sleep.

If the user responds to the safety alert or if the safety alert is otherwise attended to (the "No" branch of query task 604), then the process 600 exits and the system 100 handles the safety alert in an appropriate manner. If the process 600 confirms that the safety alert has been ignored for at least a threshold period of time (the "Yes" branch of query task 604), then the process 600 continues by taking appropriate action that is intended to notify or wake up the user. In certain embodiments, the process 600 continues by changing the default output type to an elevated output type that is more aggressive than the default output type (task 606), as described above. Next, the process 600 re-outputs the safety alert using the elevated output type (task 608). If the user continues to ignore the safety alert, then task 606 and task 608 can be repeated to continue escalating or modifying the output type, mode, or source in an appropriate manner. Thus, additional, different, louder, longer duration, more prevalent, more frequent, or more repetitive alerts or alarms can be used to escalate the manner in which the safety alert is output in an ongoing manner, in an attempt to awaken the user.

Referring again to FIG. 5, in certain implementations, the medical device 102 receives the user status data, processes the user status data to determine whether the user is sleeping, and activates a native sleep mode alerting scheme. In some embodiments, at least one ancillary control system 108 and/or at least one ancillary alerting device 110 receives the user status data, processes the user status data to determine whether the user is sleeping, and activates or controls a sleep mode alerting scheme for the medical device 102. In such embodiments, the native alerting functionality of the medical device 102 can be remotely controlled and/or an ancillary alerting device 110 can be controlled to execute the sleep mode alerting scheme. As mentioned above, controllers resident at the different components of the system 100 can be suitably configured and programmed to perform the methods and processes described here, individually or in a distributed or collective manner.

Figure 7:
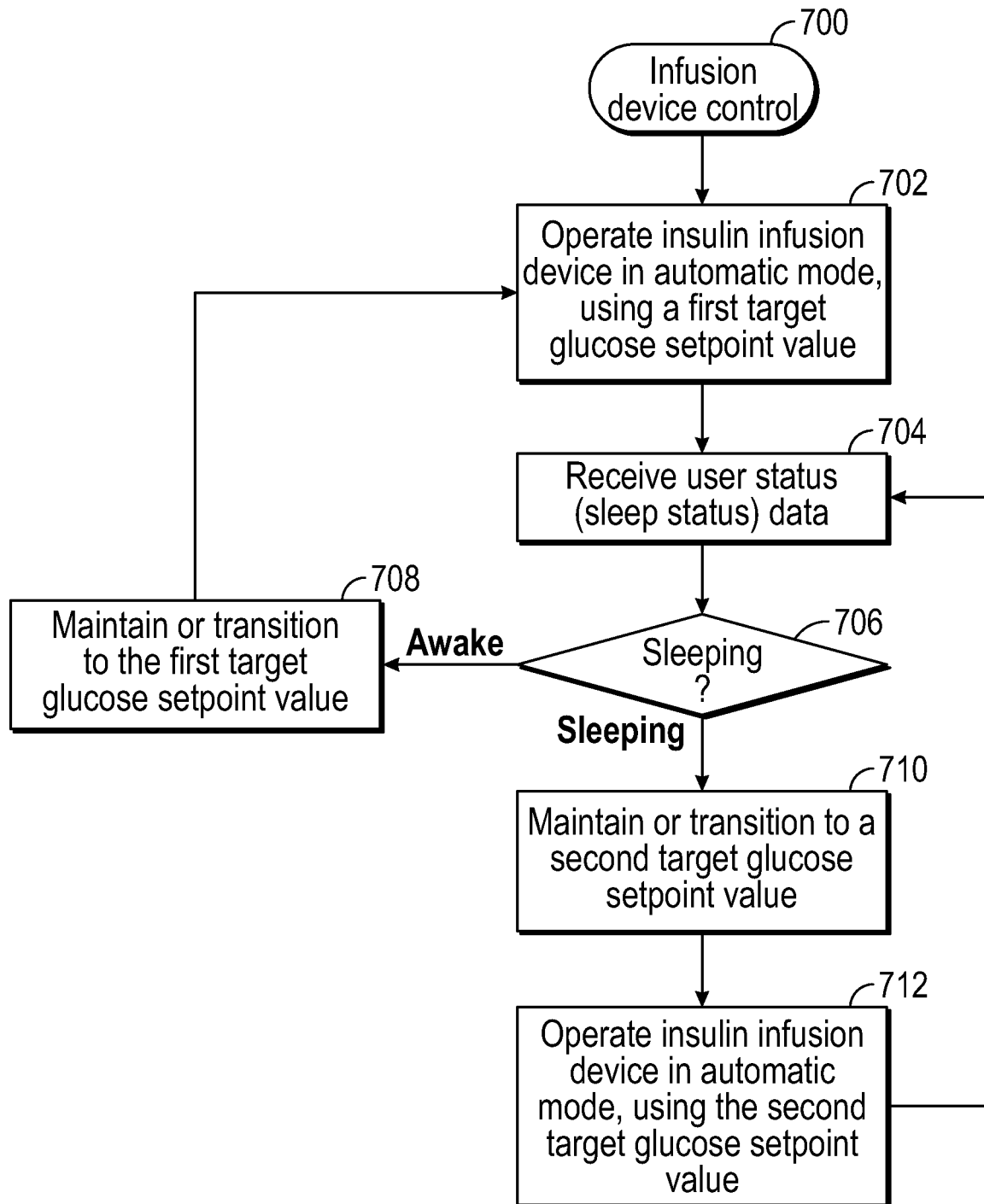
FIG. 7 is a flow chart that illustrates an insulin infusion device control process according to certain embodiments.

FIG. 7 is a flow chart that illustrates an insulin infusion device control process 700 according to certain embodiments. A number of currently available hybrid closed-loop insulin delivery systems use glucose sensor feedback control algorithms to regulate the user's blood glucose to a fixed "factory setting" setpoint, such as 120 mg/dL or 100 mg/dL. A fixed setpoint at or near 120 mg/dL represents a good target glucose for the vast majority of users that balances effective long term blood sugar control with safety (with respect to hypoglycemia). However, many users may desire a higher or lower setpoint to suit their individual needs. Disclosed here is an insulin infusion system that accommodates a variable target glucose setpoint, which can be adjusted in response to the detected sleeping status of the user. The adjustable glucose setpoint can be programmable to move to different levels at different times, such as a lower setpoint during sleeping periods to give a low fasting glucose, and a higher setpoint when the user is awake.

The process 700 represents an automated method of operating a medical device, such as the insulin infusion device 302 depicted in FIG. 3. This description assumes that the insulin infusion device is operating in an automatic mode to automatically control delivery of insulin to the user (task 702). As explained above with reference to FIG. 3, insulin delivery is controlled and regulated in accordance with various factors, sensor data, user-specific settings, etc., including a first or default target glucose setpoint value. The first target glucose setpoint value may be user-configurable, fixed by the manufacturer of the insulin infusion device, set by the user's physician or caregiver, or the like. In certain embodiments, the first target glucose setpoint value is chosen to be 120 mg/dL, although other values can be used.

The process 700 receives user status data (e.g., sleep status data) that indicates the sleeping status of a user of the medical device (task 704) and analyzes or processes at least some of the received user status data to determine whether the user is sleeping (query task 706). Task 704 is similar to task 502 of the process 500, and query task 706 is similar to query task 504 of the process 500, as described above with reference to FIG. 5. If analysis of the user status data indicates that the user is awake, then the process 700 maintains the first target glucose setpoint value as the currently active or applicable value for regulating the delivery of insulin during the automatic delivery mode (task 708). Accordingly, FIG. 7 depicts the process 700 leading back to task 702 for continued operation of the insulin infusion device.

This example assumes that the process 700 determines, from the user status data, that the user is sleeping while the insulin infusion device is operating in the automatic mode. In response to the determination that the user is sleeping, the process 700 adjusts the target glucose setpoint value by automatically transitioning (without user input) from the first target glucose setpoint value to a second target glucose setpoint value, different than the first target glucose setpoint value, for use during the automatic mode (task 710). In some examples, the second target glucose setpoint value is higher than the target glucose setpoint value. In some examples, the second target glucose setpoint value is lower than the target glucose setpoint value. The process 700 continues to operate the insulin infusion device in the automatic mode to automatically control the delivery of insulin to the user, in accordance with the second target glucose setpoint value (task 712). In some embodiments, the process 700 monitors the sleep duration of the user and initiates the transitioning to the second target glucose setpoint value when the sleep duration exceeds a threshold time period (e.g., 30 minutes, 1 hour, 2 hours, or any other period of time). In other words, adjusting the target glucose setpoint value may occur as soon as the user falls asleep, or it may be delayed until the process 700 confirms that the user has been sleeping for at least the threshold time period. In some embodiments, in addition to the duration of the sleep, the user's glucose condition can be considered. For example, if the duration of sleep is longer than the threshold time period and sensor glucose measurements are stable around the first target glucose setpoint value, then the process 700 can proceed and transition (without user input) to the second target glucose setpoint value. In some embodiments, the process 700 considers an estimated amount of plasma insulin for the user as a factor that influences whether to transition without user input to the second target glucose setpoint value. Other factors, parameters, and data that can be considered before adjusting the target glucose setpoint value include, without limitation: sensor glucose data availability; current or historical sensor glucose levels; and/or the rate of change of sensor glucose readings.

FIG. 7 shows the process 700 leading back to task 704 to receive updated or additional user status data for continued monitoring and processing during the automatic mode. If the process 700 determines (from the additional user status data) that the user is no longer sleeping, then task 708 can transition, without user input, from the second target glucose setpoint value to the first target glucose setpoint value, or to another target glucose setpoint value that is appropriate for the current user state. Thereafter, the process 700 continues to operate the insulin infusion device in the automatic mode, using the first target glucose setpoint value as a reference. If the user remains asleep, then the second target glucose setpoint value is maintained for ongoing use during the automatic mode (task 710).

Transitioning from one target glucose setpoint value to another without user input may be performed gradually or continuously over a predetermined period of time, e.g., 30 minutes, an hour, or the like. Transitioning over time in this manner assumes that the user remains asleep before and during the transition period. In certain embodiments, transitioning from one target glucose setpoint value to another without user input is performed quickly or immediately following the detection of a sleeping state. In other words, the process 700 can simply switch from one setpoint value to another in a stepwise manner.

For the example described here, the second target glucose setpoint value is lower than the first (default) target glucose setpoint value. Lowering the setpoint value is appropriate during sleeping hours because the automatic control algorithm need not consider additional factors such as eating, exercise, heartrate variations, etc. As an example, the first value may be 120 mg/dL and the second value may be 100 mg/dL, 80 mg/dL, or any value that is safe and appropriate for the particular user. The second target glucose setpoint value may be a fixed value that is set by the manufacturer of the insulin infusion device, the user, a caregiver, etc. In some embodiments, the second target glucose setpoint value is higher than the first target glucose setpoint value. As an example, the first value may be 120 mg/dL and the second value may be 130 mg/dL or any value that is safe and appropriate for the particular user.

In certain embodiments, the second target glucose setpoint value can be variable or dynamic in nature to respond to the particular sleeping status, the current user condition or glucose state, or the like. For example, the user status data provided by the sleep detection system 104 may include a sleep quality metric (as described above with reference to the process 500). The sleep quality metric generated by the sleep detection system 104 can be used to regulate or adjust the currently active second target glucose setpoint value without user input. More specifically, the second target glucose setpoint value can be adjusted as a function of the sleep quality metric generated by the sleep detection system. For example, the adjustment amount and/or the adjustment time period may be influenced by the sleep quality metric. In this regard, the target glucose setpoint value can be regulated as a function of sleep quality by monitoring non-diabetic individual(s) and mimicking the manner in which a non-diabetic person regulates glucose. Thus, physiological data, sleep-related data, and glucose response characteristics associated with non-diabetic individuals can be utilized to automatically adjust the target glucose setpoint value for diabetic users, as a function of sleep quality.

In some embodiments, the user status data provided by the sleep detection system 104 includes a sleep duration metric (as described above with reference to the process 500). The sleep duration metric generated by the sleep detection system 104 can be used to regulate or adjust the currently active second target glucose setpoint value without user input. More specifically, the target glucose setpoint value can be automatically adjusted as a function of the sleep duration metric generated by the sleep detection system. Thus, the adjustment amount and/or the adjustment time period may be influenced by the sleep duration metric. For example, if the user has only been sleeping for one hour, then the setpoint value may be adjusted by only an initial amount. If, however, the sleep duration metric indicates that the user has been continuously sleeping for an extended period of time (e.g., more than two hours or any other period of time), then it may be appropriate to lower the target glucose setpoint value by an additional amount.

As explained above, the target glucose setpoint value represents a setting, parameter, or variable of the insulin delivery control algorithm, which can be adjusted or regulated, without user input, as a function of sleep detection and/or certain sleep-related characteristics. In accordance with certain embodiments, one or more additional or alternative settings, parameters, or variables can be adjusted based on sleep detection. For example, controller gain values (which are utilized by the automatic insulin delivery control algorithm) can be adjusted as a function of sleep detection and/or certain sleep-related characteristics. In certain embodiments, the controller of an insulin infusion device employs a proportional-integral-derivative insulin feedback (PID-IFB) control algorithm designed for continuous closed-loop insulin delivery control. Some implementations of the PID-IFB control algorithm include PID gain values that are applied to an error term, a time derivative of sensor glucose term, and an integral error term (which is the integral action on historical errors between sensor glucose readings and the controller setpoint, such as 100 mg/dL). Moreover, certain implementations of the PID-IFB control algorithm calculate the IFB using time constants that can be adjusted based on sleep detection or observed/measured sleeping characteristics. In addition, certain implementations of the PID-IFB control algorithm employ a maximum insulin limit (referred to as "Umax") that governs the insulin dosage output of the control algorithm—Umax can also be adjusted based on sleep detection or observed/measured sleeping characteristics. In this regard, the controller gain values, Umax, and/or time constants can be regulated to make the controller more or less responsive to changes in sensor glucose measurements during sleeping periods.

Referring again to FIG. 5, in certain implementations, the medical device 102 receives the user status data, processes the user status data to determine whether the user is sleeping, and adjusts the target glucose setpoint value as needed. In some embodiments, at least one ancillary control system 108 receives the user status data, processes the user status data to determine whether the user is sleeping, and remotely controls the medical device 102 (as needed) to cause the adjustment of the target glucose setpoint value. For example, the ancillary control system 108 can generate and send commands, instructions, and/or control signals to the medical device 102, wherein the commands, instructions, and/or control signals cause the medical device 102 (e.g., the insulin infusion device) to transition from one target glucose setpoint value to another without user input. In such embodiments, the native insulin delivery control scheme of the insulin infusion device can be remotely controlled to respond to the sleeping status of the user. As mentioned above, controllers resident at the different components of the system 100 can be suitably configured and programmed to perform the methods and processes described here, individually or in a distributed or collective manner.

The various tasks performed in connection with a process disclosed herein may be performed by software, hardware, firmware, or any combination thereof. It should be appreciated that an embodiment of an illustrated process may include any number of additional or alternative tasks, the tasks shown in the figures need not be performed in the illustrated order, and a disclosed process may be incorporated into a more comprehensive procedure or process having additional functionality not described in detail herein. Moreover, one or more of the tasks shown in a figure could be omitted from an embodiment of the depicted process as long as the intended overall functionality remains intact.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. An automated method of controlling alerts associated with operation of a medical device, the method comprising:
   receiving user status data that indicates sleeping status of a user of the medical device, the user status data generated by a sleep detection system;
   determining, from the user status data, that the user is sleeping;
   in response to the determining, activating a sleep mode alerting scheme of the medical device; and
   after activating the sleep mode alerting scheme, controlling generation and outputting of alerts associated with operation of the medical device in accordance with the sleep mode alerting scheme.

2. The method of claim 1, wherein the sleep mode alerting scheme silences at least one alert while the user is asleep.

3. The method of claim 1, wherein the sleep mode alerting scheme queues at least one alert for subsequent presentation to the user.

4. The method of claim 1, wherein the sleep mode alerting scheme delays outputting of at least one alert while the user is asleep.

5. The method of claim 1, wherein the sleep mode alerting scheme changes a default output type, for at least one alert, to an elevated output type that is more aggressive than the default output type.

6. The method of claim 5, wherein:
   the default output type is associated with outputting of the at least one alert by a default alerting device; and
   the elevated output type is associated with outputting of the at least one alert by an ancillary alerting device that is different than the default alerting device.

7. The method of claim 1, further comprising:
   outputting a safety alert, using a default output type, after determining that the user is sleeping;
   confirming that the safety alert has been ignored for at least a threshold period of time;
   in response to the confirming, changing the default output type to an elevated output type that is more aggressive than the default output type; and
   re-outputting the safety alert using the elevated output type.

8. The method of claim 1, wherein:
   the user status data includes a sleep quality metric for the user, the sleep quality metric generated by the sleep detection system; and
   the sleep mode alerting scheme regulates generation or outputting of the alerts as a function of the sleep quality metric.

9. The method of claim 1, wherein:
   the user status data includes a sleep duration metric for the user, the sleep duration metric generated by the sleep detection system; and
   the sleep mode alerting scheme regulates generation or outputting of the alerts as a function of the sleep duration metric.

10. The method of claim 1, wherein:
    the sleep detection system is separate and distinct from the medical device; and
    the medical device performs the receiving, determining, activating, and controlling steps.

11. The method of claim 1, wherein:
    the medical device comprises the sleep detection system; and the medical device performs the receiving, determining, activating, and controlling steps.

12. The method of claim 1, wherein the receiving, determining, activating, and controlling steps are performed by at least one ancillary control system that remotely controls operation of the medical device.

13. A medical device that regulates delivery of medication to a user, the medical device comprising:
a fluid pump mechanism;
at least one controller that regulates operation of the fluid pump mechanism to deliver a fluid medication from the medical device; and
at least one memory element associated with the at least one controller, the at least one memory element storing processor-executable instructions configurable to be executed by the at least one controller to perform a method of controlling operation of the medical device, the method comprising:
receiving user status data that indicates sleeping status of the user, the user status data generated by a sleep detection system;
determining, from the user status data, that the user is sleeping;
in response to the determining, activating a sleep mode alerting scheme of the medical device; and
after activating the sleep mode alerting scheme, controlling generation and outputting of alerts associated with operation of the medical device in accordance with the sleep mode alerting scheme.

14. The medical device of claim 13, wherein the medical device receives the user status data directly from the sleep detection system.

15. The medical device of claim 13, wherein:
the medical device is an insulin infusion device; and
the fluid medication comprises insulin.

16. The medical device of claim 13, wherein the sleep mode alerting scheme silences at least one alert while the user is asleep.

17. The medical device of claim 13, wherein the sleep mode alerting scheme changes a default output type, for at least one alert, to an elevated output type that is more aggressive than the default output type.

18. The medical device of claim 17, wherein:
the default output type is associated with outputting of the at least one alert by the medical device; and
the elevated output type is associated with outputting of the at least one alert by an ancillary alerting device other the medical device.

19. A system comprising:
a medical device that regulates delivery of medication to a user;
a sleep detection system configured to generate user status data that indicates sleeping status of the user, and configured to communicate the user status data; and
at least one controller that controls alerts associated with operation of the medical device, the at least one controller configured to:
receive the user status data generated by the sleep detection system;
determine, from the user status data, that the user is sleeping;
in response to determining that the user is sleeping, activating a sleep mode alerting scheme of the medical device; and
after activating the sleep mode alerting scheme, control generation and outputting of alerts associated with operation of the medical device in accordance with the sleep mode alerting scheme.

20. The system of claim 19, wherein the medical device comprises the at least one controller.

21. The system of claim 19, wherein the sleep detection system comprises a gesture-based, motion-based, or activity-based detection system.

22. The system of claim 19, wherein the medical device comprises the sleep detection system.

* * * * *